US012601104B2

(12) United States Patent
Cunningham, III

(10) Patent No.: US 12,601,104 B2
(45) Date of Patent: Apr. 14, 2026

(54) SPORTS EQUIPMENT DRYING DEVICE

(71) Applicant: Glenn Cunningham, III, LaGrange, GA (US)

(72) Inventor: Glenn Cunningham, III, LaGrange, GA (US)

( * ) Notice: Subject to any disclaimer, the term of this patent is extended or adjusted under 35 U.S.C. 154(b) by 0 days.

(21) Appl. No.: 18/744,183

(22) Filed: Jun. 14, 2024

(65) Prior Publication Data

US 2024/0328067 A1 Oct. 3, 2024

Related U.S. Application Data

(63) Continuation of application No. 17/338,878, filed on Jun. 4, 2021, now Pat. No. 12,037,737.

(60) Provisional application No. 63/035,064, filed on Jun. 5, 2020.

(51) Int. Cl.
| | |
|---|---|
| *D06F 58/26* | (2006.01) |
| *A61L 2/20* | (2006.01) |
| *D06F 58/10* | (2006.01) |
| *D06F 58/46* | (2020.01) |
| *A61L 2/202* | (2026.01) |

(52) U.S. Cl.
CPC ............ *D06F 58/263* (2013.01); *D06F 58/10* (2013.01); *D06F 58/46* (2020.02); *A61L 2/202* (2013.01); *A61L 2202/122* (2013.01); *A61L 2202/26* (2013.01)

(58) Field of Classification Search
CPC ........ D06F 58/263; D06F 58/46; D06F 58/10; A61L 2/202; A61L 2202/122; A61L 2202/26

USPC .......................................................... 34/549
See application file for complete search history.

(56) References Cited

U.S. PATENT DOCUMENTS

| | | | |
|---|---|---|---|
| 2,561,652 | A | 7/1951 | Doolan |
| 2,752,694 | A | 7/1956 | Mccormick |
| 5,555,640 | A | 9/1996 | Ou |
| 6,018,885 | A | 2/2000 | Hill |
| 6,134,806 | A | 10/2000 | Dhaemers |
| 6,263,591 | B1 | 7/2001 | La Porte |
| 6,796,053 | B2 | 9/2004 | Lurie |
| 6,889,449 | B2 | 5/2005 | Silver |

(Continued)

FOREIGN PATENT DOCUMENTS

| | | | | | |
|---|---|---|---|---|---|
| CN | 101240496 | A | * | 8/2008 | ............. D06F 58/14 |
| WO | WO-2008064236 | A2 | * | 5/2008 | ............. A61L 2/202 |

*Primary Examiner* — Stephen M Gravini
(74) *Attorney, Agent, or Firm* — Boudwin Intellectual Property Law, LLC; Daniel Boudwin

(57) ABSTRACT

A drying device is provided. The device includes a frame having a base portion with a plurality of supporting castor wheels. A front support and a rear support extend upwardly from opposing ends of the base portion. A horizontal bar is affixed between the upper ends of the front and rear supports. The horizontal bar may include various configurations of hooks and extending rods for hanging sports equipment and garments for storage and drying. The height of horizontal bar can be adjusted by a push button adjuster. A flexible transparent cover is removably securable around the frame. A forced air heater is disposed on the base portion of the frame. The forced air heater includes a temperature control, a timer control, and a tip-over switch. The device further includes an ozone generator with a timer control for deodorizing the contents of the bag during the drying process.

19 Claims, 4 Drawing Sheets

(56)            References Cited

U.S. PATENT DOCUMENTS

| | | | | |
|---|---|---|---|---|
| 8,387,271 B2 * | 3/2013 | Shami | .................... | A45D 20/12 |
| | | | | 132/211 |
| 8,667,707 B2 * | 3/2014 | Date | .................... | D06F 58/203 |
| | | | | 211/195 |
| 8,844,158 B2 * | 9/2014 | Dehn | .................... | D04H 1/407 |
| | | | | 34/282 |
| 8,997,372 B2 | 4/2015 | Cennon | | |
| 9,498,039 B2 * | 11/2016 | Matsui | .................. | A45D 20/12 |
| 9,689,609 B2 | 6/2017 | Lee et al. | | |
| 9,743,739 B2 * | 8/2017 | Parisi | ........................ | A61L 2/10 |
| 10,100,458 B2 * | 10/2018 | Stewart | ............. | A63B 71/0036 |
| 10,876,792 B2 * | 12/2020 | Zielinski | ................... | F26B 3/20 |
| 11,513,478 B2 * | 11/2022 | Kim | .................... | G05B 13/027 |
| 11,713,924 B2 * | 8/2023 | Zielinski | ................ | F26B 23/04 |
| | | | | 34/92 |
| 11,832,697 B2 | 12/2023 | Grimes | | |
| 12,037,737 B2 * | 7/2024 | Cunningham, III | .... | D06F 58/14 |
| 12,290,212 B1 * | 5/2025 | Lin | ...................... | A47K 10/025 |
| 12,290,227 B2 * | 5/2025 | White-Petteruti | ...... | A47L 19/00 |
| 2004/0003511 A1 | 1/2004 | Silver | | |
| 2005/0160617 A1 | 7/2005 | Fouts, II | | |
| 2007/0086914 A1 | 4/2007 | Antinozzi | | |
| 2008/0118411 A1 | 5/2008 | D'Arinzo | | |
| 2008/0168675 A1 | 7/2008 | Garman et al. | | |
| 2012/0159807 A1 | 6/2012 | Vezina et al. | | |
| 2014/0325863 A1 | 11/2014 | Blum | | |
| 2021/0381156 A1 | 12/2021 | Cunningham, III | | |
| 2024/0328067 A1 * | 10/2024 | Cunningham, III | .. | D06F 58/263 |

* cited by examiner

SPORTS EQUIPMENT DRYING DEVICE

CROSS REFERENCE TO RELATED APPLICATIONS

This application claims the benefit of U.S. Non-provisional application Ser. No. 17/338,878 filed on Jun. 4, 2021, as a continuation, and to U.S. Provisional Application No. 63/035,064 filed on Jun. 5, 2020. The above identified patent applications are herein incorporated by reference in their entirety to provide continuity of disclosure.

BACKGROUND OF THE INVENTION

The present invention relates to a drying apparatus. More specifically, the present invention provides a frame that has at least one rack that allows for athletic equipment and other objects to dry with the assistance of a forced air heater and an ozone generator.

Many sports require that players wear protective equipment. The protective equipment limits the chances that the player suffers an injury. The protective equipment is often in direct contact with the player's skin or separated be a thin layer of clothing. When partaking in the sport, the player will produce high amounts of sweat. While playing the sport, the sweat produced by the player can be absorbed into the protective equipment. This can leave the protective equipment damp and wet when the player removes it following the game. Often times, the player will place the wet protective equipment directly into a sports bag. When the protective equipment is not properly dried, the protective equipment may develop an odor or can even have bacteria grow on the equipment. When the protective equipment contains an odor or bacteria it can lead to the player having to purchase new protective equipment.

For contact sports like ice hockey, lacrosse, and football, the protective equipment can be bulky and large. The design of the protective equipment used in these sports allows the players to have enough protection while they play the sport but limit the amount of drying methods available. Specifically, the size of the protective equipment prohibits them from being dried in a standard tumble dryer. The standard tumble dryers do provide an efficient and effective means to dry clothing and other items that fit therein. The heated air that is sent through the clothing allows for them to be completely dried. Without the ability to have similar results with the protective equipment, individuals must find alternative drying methods to reduce the risk of bacteria and prevent an odor to their protective equipment.

Players may choose to naturally dry their protective equipment following use. The natural drying process can be time consuming. This leaves some individuals to place their protective equipment in a storage bag even if the protective equipment has not completely dried when naturally air drying the protective equipment. Even though these individuals do have the intention of drying the protective equipment before storing it, the natural drying process may take such a long amount of time that the protective equipment can still develop an odor or bacterial growth when it is not completely dried.

Additionally, it may be difficult for the individual to have a proper space to air dry their protective equipment. Many individuals that play these sports might not have the outdoor space to air dry their protective equipment or live in an apartment building or dormitory and have only the interior space to air dry their protective equipment. In such situations, they might have to lay their protective equipment on furniture or the floor. Having to lay the wet protective equipment within the interior space of their apartment or dormitory may prevent them from effectively drying due to the lack of air circulation. Moreover, the wet protective equipment could cause damage to the furniture that it is placed upon and leave an odor within the individual's living space. This can make the individual's living environment intolerable to stay in or can lead to bacteria growing on the furniture. These individuals lack the ability to dry their protective equipment.

Therefore, there is a defined need amongst the known prior art references for a drying frame that provides enhanced air flow to effectively and effectively dry used athletic protective equipment.

SUMMARY OF THE INVENTION

In view of the foregoing disadvantages inherent in the known types of drying devices now present in the known art, the present invention provides a new drying apparatus having a wheel supported frame with upper supporting rods and hooks, as well as a transparent cover, timer and temperature control equipped heaters, and a timer equipped ozone generator.

It is therefore an object of the present invention to provide a drying apparatus that allows a user to place worn protective equipment upon supporting rods and the hooks to dry. Due to the shape and size of the protective equipment that is commonly used for contact sports, there are a lack of sufficient drying methods. Specifically, protective equipment will not be able to fit into standard tumble drying machines. Standard tumble drying machines typically are used to completely dry all items that are placed therein. Without the ability to use standard drying machines for the protective equipment, users will need the drying apparatus in order to have an efficient means to dry their protective equipment after they are used. The use of the drying apparatus limits the chances that the protective equipment develops bacteria and helps prevent the protective equipment from having an odor.

Another aspect of the present invention is the wheel supported frame. Users that lack the proper outdoor space to allow their protective equipment to naturally dry often are required to lay their wet protective equipment within their living space, this includes placing it on furniture. Users without the ability to naturally dry their protective equipment because of a lack of space, need a device that allows them to dry their protective equipment within the confines of their living space. The drying device will give the users a structure to place their protective equipment upon inside their living space. Moreover, the wheel supported frame will limit the moisture and odor permeation onto the furniture and other areas of the user's living space. Depending on the amount of protective equipment that a user must dry, the support frame may be too heavy to transport to different areas of their living space. Providing the user with a wheel support frame allows them to place the protective equipment on the frame and transport support frame to another section of their living area. In this way, the user can easily position the support frame within their living space in such a way that does not create an obstacle for themselves or others.

Another aspect of the present invention is the timer and temperature control equipped heater. The timer and temperature control equipped heater produce air that circulates around the items placed on the drying device, creating a using natural convection. When the air is heated, the forced air heater can dry the items placed on the drying device. The temperature control permits the user to set the temperature of the air that the forced air heater produces. This will prevent the protective equipment, or other items, from being damage due to high air temperatures. The timer control allows for the user to set a predetermined amount of time that the forced air heater will produce the air. Users may leave the drying device unsupervised for an extended period of time and the timer control will help prevent a potential hazard from occurring.

Yet another aspect of the present invention is the timer equipped ozone generator. The timer equipped ozone generator produces an ozone gas by breaking oxygen molecules into individual atoms, which then connect to another oxygen molecule in the air to form ozone. The ozone gas purifies the air in order to mask the odor on the items that are being dried. The timer control can turn off the ozone generator after a pre-determined time is set. This will allow the ozone generator to mask the odor without saturating the air with ozone gas.

Yet another aspect of the present invention is the transparent cover. The transparent cover is placed over the drying device and the items thereon and allows the heater and the ozone generator to function in an enclosed area. When in the enclosed area, the heater and the ozone generator function more efficiently. This will allow the protective equipment placed upon the drying device and under the transparent cover to become completely dry and in a short amount of time. The transparent cover allows the drying device to dry the protective equipment for suitable storage without the chance for bacteria to develop or an odor to remain.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
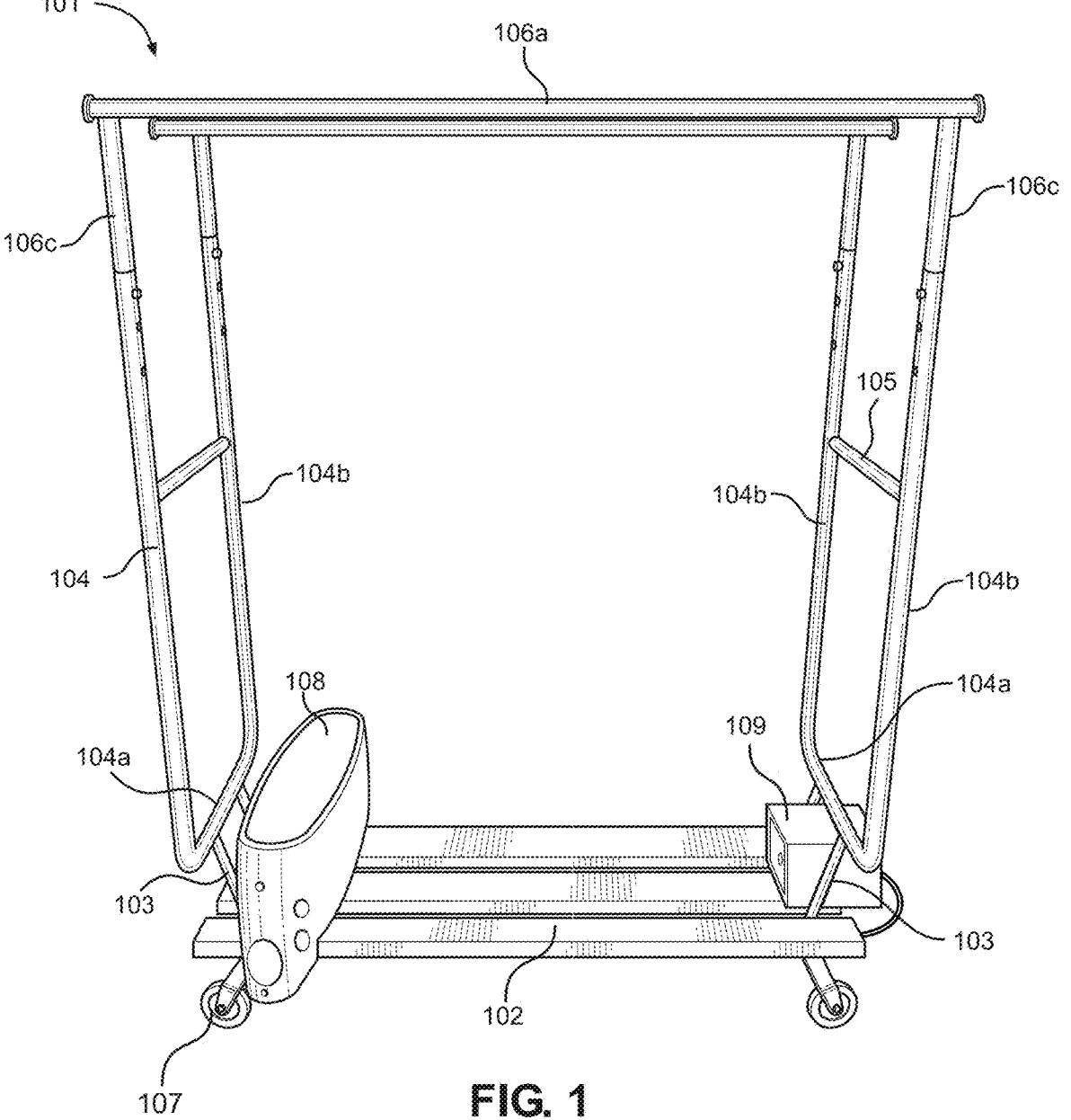
FIG. 1 shows a perspective view of an embodiment of the drying device.

Reference is made herein to the attached drawings. Like reference numerals are used throughout the drawings to depict like or similar elements of the sports equipment drying device. For the purposes of presenting a brief and clear description of the present invention, the preferred embodiment will be discussed is the sports equipment drying device with two supporting racks on opposing sides of a base, a forced air heater, and an ozone generator. The figures are intended for representative purposes only and should not be limiting in any respect.

FIG. 1 shows a perspective view of an embodiment of a drying device. The drying device 101 comprises a base 102, a plurality of support lifts 103, and a plurality of supporting castor wheels 107. The base 102 further comprises a top face and a bottom face. The plurality of supporting castor wheels 107 are disposed on the bottom face of the base 102. The plurality of support lifts 103 are disposed on the top face of the base 102. The plurality of support lifts 103 are paired on opposing ends of the base 102.

The plurality of support lifts 103 are connected to at least one support. This embodiment of the drying device 101 comprises a front support and a rear support. Each support comprises a horizontal base 104a, a pair of parallel vertical bars 104b, and a horizontal support bar 105. The horizontal base 104a rests upon the pair of support lifts 103. The pair of parallel vertical bars 104b are disposed on opposing ends of the horizontal base 104a. In some embodiments, each vertical bar 104b is hollow. A horizontal support bar 105 is sandwiched between the pair of parallel vertical bars 104b. The horizontal support bar 105 provides additional support to the pair of parallel vertical bars 104b. The front support and the rear support are located on opposing ends of the base 102.

A horizontal bar 106a is disposed on top of a pair of telescopic vertical bars 106c. The ends of the horizontal bar 106a protrude out from the connection point of each telescopic vertical bar 106c. A first telescopic vertical bar is inserted into a first vertical bar on the front support. A second telescopic vertical bar is inserted into a first vertical bar on the rear support. A first horizontal bar will couple the first vertical bar on the front support with the first vertical bar on the rear support, via the corresponding telescopic vertical bars. A second horizontal bar will couple a second vertical bar on the front support with a second vertical bar on the rear support, via a set of corresponding telescopic vertical bars. The first horizontal bar and the second horizontal bar are horizontally parallel from each other.

A forced air heater 108 is disposed on the top face of the base 102. The forced air heater 108 includes a temperature control, a timer control, and a tip-over switch. The forced air heater 108 produces and distributes air through a closed area. The air produced the forced air heater 108 circulates around the items placed on the drying device 101 creating a using natural convection. When the air is heated, the forced air heater 108 can function as a dryer for the items placed on the drying device 101. The temperature control permits user to set the temperature of the air that the forced air heater 108 produces. Depending on the items that the user intends to dry in the drying device 101, the user will want to adjust the temperature of the air so that the items do not get damaged from high air temperatures. The timer control allows for the user to set a predetermined amount of time that the forced air heater 108 will function. Users may leave the drying device 101 while their items are being dried. Leaving the drying device 101 unsupervised for an extended period of time while it is operating may be a potential hazard. However, the timer control allows the user to walk away from the drying device 101 with limited worry about potential hazards because the forced air heater 108 will turn off after a predetermined amount of time.

Moreover, the forced air heater includes the tip-over switch. The tip-over switch is disposed on the forced air heater 108. The tip-over switch senses movement of the forced air heater 108 above and below a horizontal axis. If the forced air heater 108 is tilted more than a specified angle, the tip-over switch will deactivate the forced air heater 108. The tip-over switch will prevent any hazards arising from the forced air heater 108 falling over or making contact with the area surrounding the drying device 101. This feature will provide users with the assurance that if they were to walk away from the drying device 101 while it is in use, and if forced air heater 108 were to have its position altered, the forced air heater 108 will deactivate, limiting the chance that a dangerous hazard will result.

An ozone generator 109 is disposed on the top face of the base 102. The ozone generator 109 includes a timer control. The ozone generator 109 produces an ozone gas by breaking oxygen molecules into individual atoms, which then connect to another oxygen molecule in the air to form ozone. The ozone gas purifies the air in closed spaces. Specifically, the ozone generator 109 will remove organic compounds from the air. The produced ozone gas can mask the odor on the items that are being dried. The timer control can turn off the ozone generator 109 after a pre-determined time is set. This will allow the ozone generator 109 to mask the odor without saturating the air with ozone gas.

Figure 2:
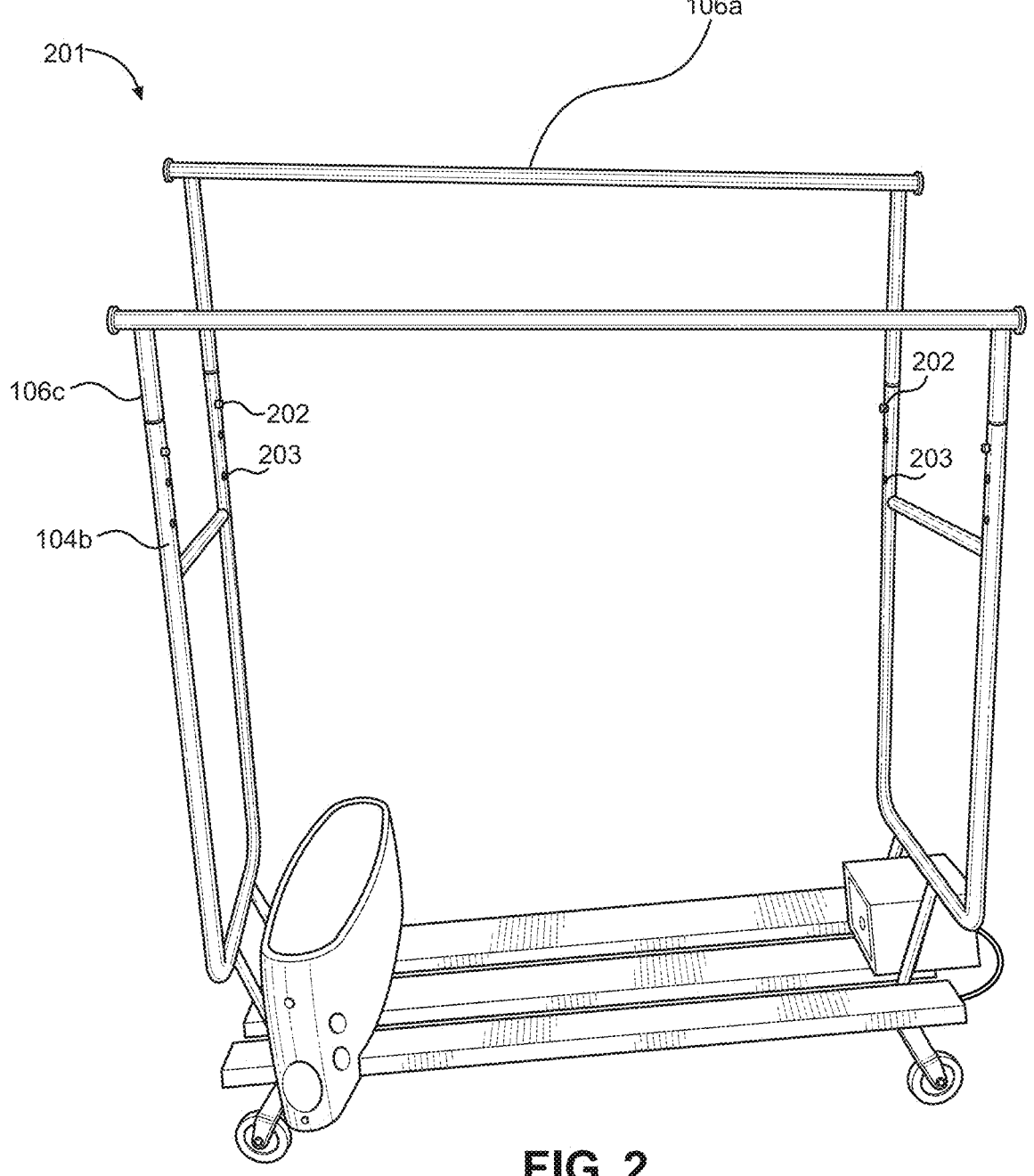
FIG. 2 shows a perspective view of an embodiment of the drying device.

FIG. 2 shows a perspective view of an embodiment of a drying device. The drying device 201 comprises at least one horizontal bar 106*a*. Each horizontal bar 106*a* is disposed on top of a pair of telescopic vertical bars 106*c*. An adjusting device is disposed on each telescopic vertical bar 106*c*. In this embodiment of the drying device 201, the adjusting device is a push button adjuster 202. The pair of telescopic vertical bars 106*c* are inserted into the hollow pair of parallel vertical bars 104*b*. Moreover, a plurality of apertures 203 are disposed vertically along each parallel vertical bar 104*b*. When the pair of telescopic vertical bars 106*c* are inserted into the pair of parallel vertical bars 104*b*, the push button adjuster 202 is disengaged. When one of the plurality of apertures 203 is over the push button adjuster 202, the push button adjuster 202 will inserted through the aperture. When the push button adjuster 202 passes through an aperture, the telescopic vertical bar 106*c* will be locked into place. To unlock the telescopic vertical bar 106*c*, a user may push the push button adjuster 202 and alter the position of the telescopic vertical bars 106*c*. Moreover, a user can adjust the height of the at least one horizontal bar 106*a* by pushing the push button adjuster 202 and adjusting the height of the telescopic vertical bars 106*c* relative to the pair of parallel vertical bars 104*b*. When the telescopic vertical bars 106*c* are in the desired position, the user will line the push button adjuster 202 in place to pass through the aperture, to secure the horizontal bar 106*a* for use.

Figure 3:
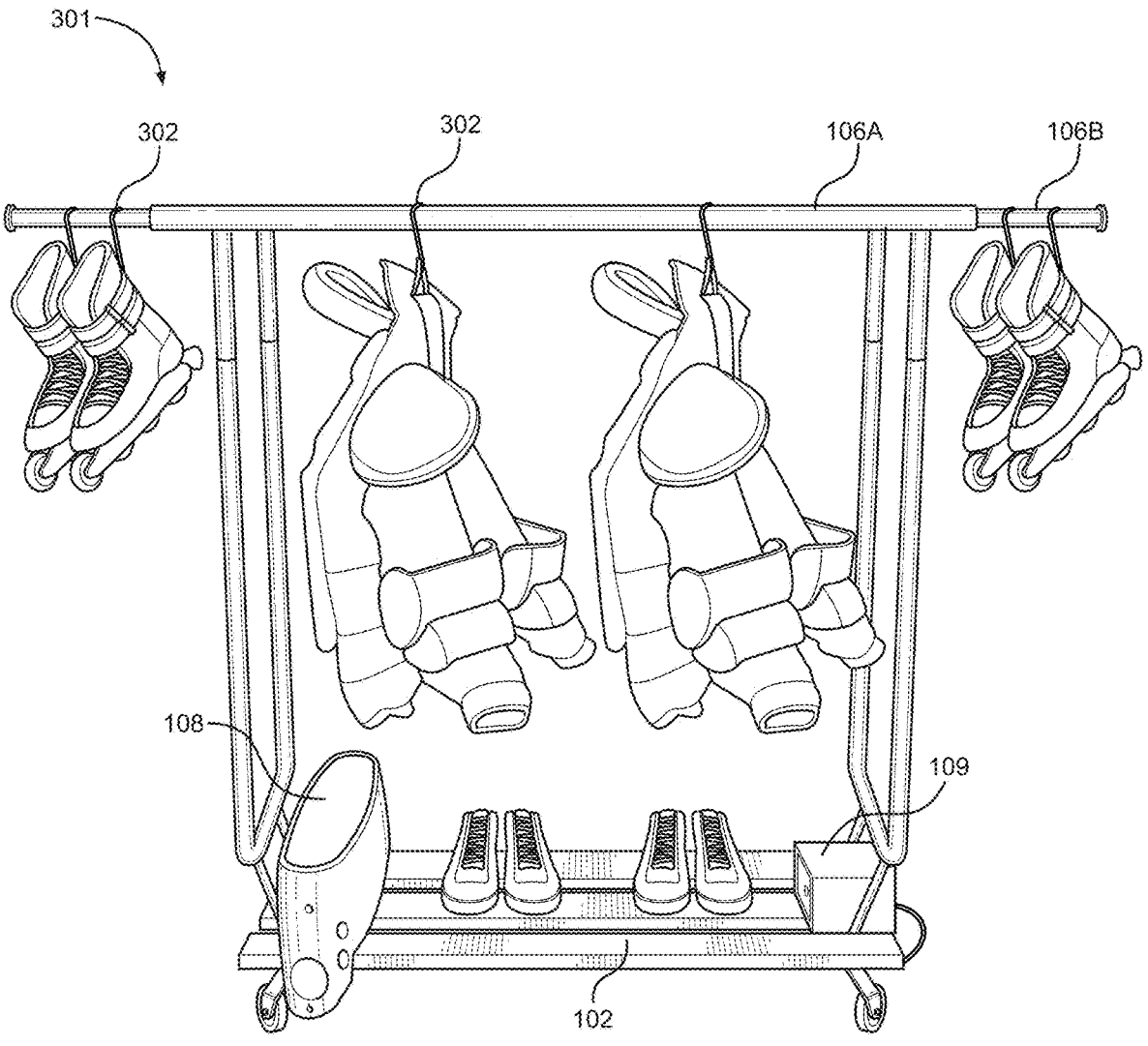
FIG. 3 shows a perspective view of an embodiment of the drying device in use.

FIG. 3 shows a perspective view of an embodiment of a drying device in use. The horizontal bar 106*a* further comprises a pair of extending rods 106*b*. Each extending rod 106*b* is disposed on opposing ends of the horizontal bar 106*a*. Users can selectively engage the pair of extending rods 106*b* by pulling the ends of the pair extending rods 106*b* away from the horizontal bar 106*a*. The pair of extending rods 106*b* provides additional length to the horizontal bar 106*a* to place more items thereon. If the additional length to the horizontal bar 106*a* is not required, the user can selectively disengage the pair of extending rods 106*b* by pushing the ends of the pair extending rods 106*b* towards the horizontal bar 106*a*.

In use, users may place a plurality of hooks 302 upon the horizontal bar 106*a* and the pair of extending rods 106*b*. The plurality of hooks 302 comprise an attaching end and a hook end. The attaching end encircles either the horizontal bar 106*a* or the pair of extending rods 106*b*. The plurality of hooks 302 are selectively attached to the horizontal bar 106*a* or the pair of extending rods 106*b* and maybe positioned anywhere along the horizontal bar 106*a* or the pair of extending rods 106*b*. The hook end permits protective equipment, clothing, etc. that needs to be dried to be placed thereon. Additionally, users may place items directly on either the horizontal bar 106*a* or the pair of extending rods 106*b*. Moreover, users may place additional items directly upon the base 102. While items are placed upon the drying device 301, they can properly dry naturally or with the use of the forced air heater 108 and ozone generator 109.

Figure 4:
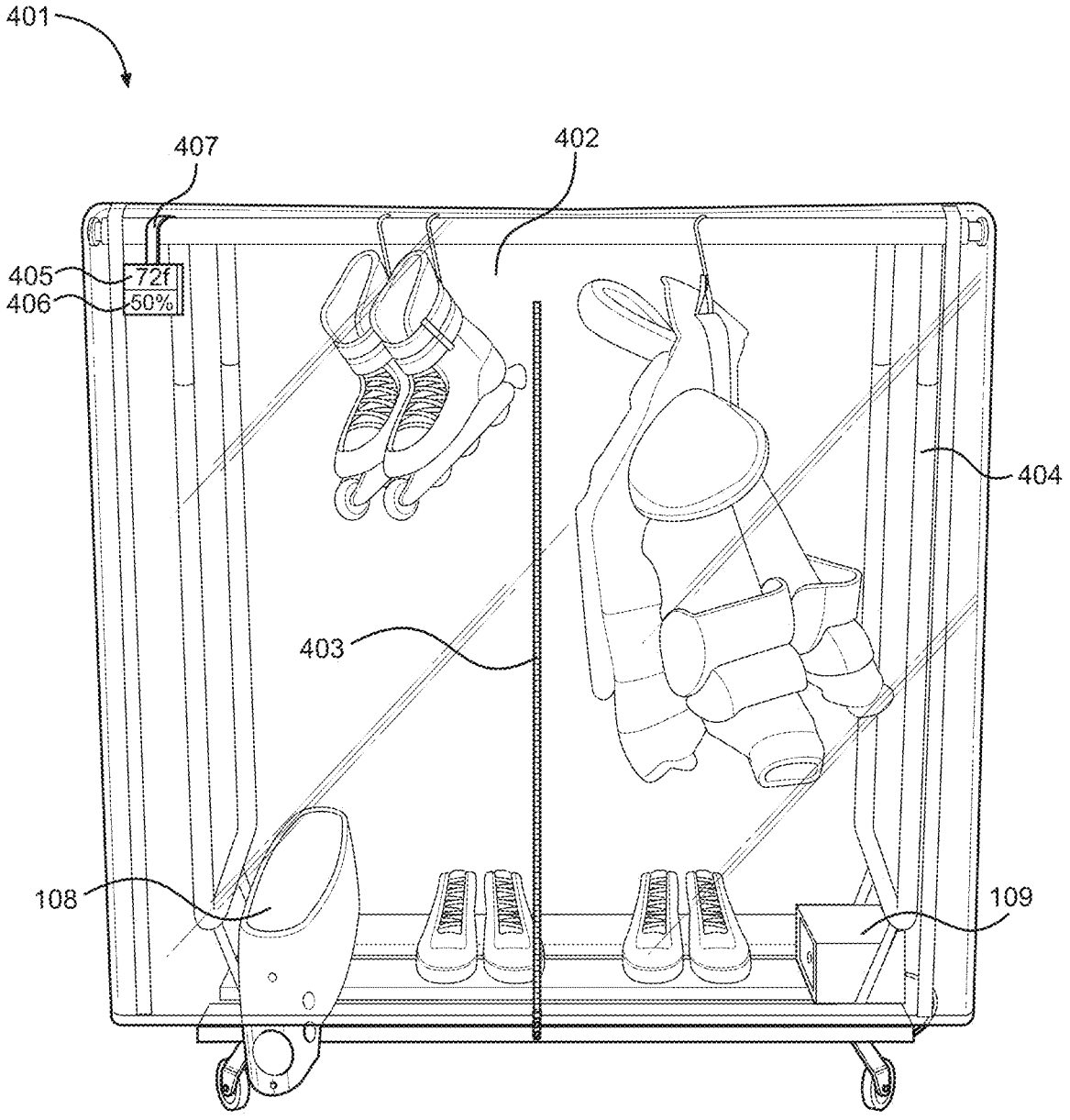
FIG. 4 shows a perspective view of an embodiment of the drying device in use.

FIG. 4 shows a perspective view of an embodiment of a drying device in use. The drying device 401 further includes a flexible transparent cover 402. The flexible transparent cover 402 comprises a body and a fastener. The body of the flexible transparent cover 402 includes a top side, a back side, a front side, and a pair of opposing sides. The front side may be open. The open front side 404 further comprises a fastener. In one embodiment of the flexible transparent cover 402, the fastener is a zipper 403. The flexible transparent cover 402 is placed over the drying device 401 and the items thereon. The fastener closes the open front side 404 of the flexible transparent cover 402 securing it around the drying device 401 and the drying items. When the flexible transparent cover 402 covering is closed, it allows the forced air heater 108 and ozone generator 109 to function efficiently in an enclosed area to drying and deodorizing the drying items. In another embodiment of the flexible transparent cover 402, there is no open front side. The flexible transparent cover 402 will be pulled over the top of the drying device 401 and the drying items thereon.

The drying device further comprises a thermometer 405 and a hygrometer 406. The thermometer 405 measures temperature in the air or in a confined space. The thermometer 405 includes a sensor that detects the temperature and a display that allows a user to view the temperature value. The hygrometer 406 measures the amount of water vapor that in the air or in a confined space. The hygrometer 406 includes a display that allows the user to view the humidity level. When the flexible transparent cover 402 is placed over the drying device 401 and the drying items thereon, the user will want to know the temperature and the humidity that is underneath the flexible transparent cover 402. The thermometer 405 and the hygrometer 406 are affixed to a hook 407. The hook 407 is securable about the horizontal bar. In another embodiment of the drying device 401, the user can set a temperature for the thermometer 405 and a humidity range for the hygrometer 406. The ability to set both the temperature and the humidity of the drying device 401 will allow the user to prevent any damage occurring to the items that are place upon the drying device 401. Moreover, the temperature and the humidity range may be set via an electronic device application. The user will be able to access the electronic device application and determine the temperature and the humidity range their items will be in when the flexible transparent cover 402 is secured. The user will receive a notification from the electronic device application when either the temperature and or the humidity range falls outside the desired range.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A drying device, comprising:

a base, having a top face and a bottom face;

a plurality of supporting castor wheels; disposed on the bottom face of the base;

a support frame, including a plurality of support lifts, a front support, a rear support, and at least one horizontal bar;

wherein the front support and the rear support of the support frame each includes a horizontal base, a pair of parallel vertical bars, and a horizontal support bar;

a plurality of apertures disposed on a top of each of the parallel vertical bars;

wherein each of the at least one horizontal bar is disposed on top of a pair of telescopic vertical bars;

wherein the pair of telescopic vertical bars are connected to a front support parallel vertical bar and a rear support parallel vertical bar;

wherein each of the at least one horizontal bar includes a pair of extending rods;

a heater disposed on the top face of the base;

a flexible cover removably secured around the support frame;

wherein the plurality of support lifts are disposed on opposing ends of the top face of the base, whereby the front support is disposed on a first set of support lifts and the rear support is disposed on a second set of support lifts; and wherein the pair of parallel vertical bars are disposed on opposing ends of the horizontal base and the horizontal support bar is sandwiched between the pair of parallel vertical bars.

2. The drying device of claim 1, wherein each of the parallel vertical bars is hollow.

3. The drying device of claim 1, wherein each of the telescopic vertical bars includes an adjusting device.

4. The drying device of claim 3, wherein the adjusting device is a push button adjuster.

5. The drying device of claim 4, wherein the push button adjuster protrudes through an aperture disposed along a top of each parallel vertical bar.

6. The drying device of claim 1, wherein the pair of extending rods are disposed on opposing ends of each horizontal bar.

7. The drying device of claim 1, wherein the pair of extending rods are selectively engaged by pulling an end of the pair of extending rods away from the horizontal bar and selectively disengage by pushing the ends of the pair of extending rods towards the horizontal bar.

8. The drying device of claim 1, wherein the flexible cover includes an open body having a top side, a back side, a front side, and a pair of opposing sides.

9. The drying device of claim 8, wherein the flexible cover is placed over the drying device.

10. The drying device of claim 8, wherein the front side of the open body of the flexible cover includes a fastener.

11. The drying device of claim 10, wherein the fastener is a zipper; disposed along the front side of the open body of the flexible cover.

12. The drying device of claim 10, wherein the flexible cover is placed over the drying device and the fastener closes the open body about the drying device.

13. The drying device of claim 1, wherein a first horizontal bar and a second horizontal bar are horizontally parallel from each other.

14. The drying device of claim 13, wherein the first horizontal bar, the second horizontal bar, and the pair of extending rods support a plurality of hooks.

15. The drying device of claim 1, wherein a thermometer and a hygrometer are affixed to one of the plurality of hooks securable about the horizontal bar.

16. The drying device of claim 1, wherein the heater includes a temperature control, a timer control, and a tip-over switch.

17. The drying device of claim 1, wherein the ozone generator includes a timer control.

18. The drying device of claim 1, wherein the front support is disposed on one pair of the plurality of support lifts and the rear support is disposed on another pair of the plurality of support lifts.

19. The drying device of claim 1, wherein an ozone generator is disposed on the top face of the base.

* * * * *